United States Patent [19]
Tillinghast, III; Theodore V. et al.

[11] Patent Number: 5,458,565
[45] Date of Patent: Oct. 17, 1995

[54] OSTEOARTHRITIC KNEE BRACE

[75] Inventors: Theodore V. Tillinghast, III, Cardiff; Charles A. Bastyr, San Diego; Richard E. Gildersleeve, Escondido, all of Calif.

[73] Assignee: Smith & Nephew Donjoy Inc., Carlsbad, Calif.

[21] Appl. No.: 191,410

[22] Filed: Feb. 3, 1994

Related U.S. Application Data

[63] Continuation-in-part of Ser. No. 104,184, Aug. 10, 1993, Pat. No. 5,415,625, which is a continuation-in-part of Ser. No. 907,160, Jul. 1, 1992, Pat. No. 5,316,547.

[51] Int. Cl.⁶ ............................................. A61F 5/00
[52] U.S. Cl. ..................................... 602/26; 602/16
[58] Field of Search ................................. 602/5, 16, 26, 602/13; 128/898

[56] References Cited

U.S. PATENT DOCUMENTS

| | | |
|---|---|---|
| 2,531,074 | 11/1950 | Miller .................... 128/DIG. 20 X |
| 3,581,741 | 6/1971 | Rosman . |
| 3,581,741 | 6/1971 | Rosman .................... 602/26 X |
| 3,669,105 | 6/1972 | Castiglia .................... 602/26 X |
| 3,902,482 | 9/1975 | Taylor . |
| 3,945,047 | 3/1976 | Jarrell, Jr. . |
| 3,955,565 | 5/1976 | Johnson, Jr. . |
| 3,958,569 | 5/1976 | Vosburgh . |
| 4,201,203 | 5/1980 | Applegate .................... 602/26 |
| 4,219,892 | 9/1980 | Rigdon .................... 602/26 X |
| 4,280,489 | 7/1981 | Johnson, Jr. . |
| 4,287,920 | 9/1981 | Johnson, Jr. . |
| 4,361,142 | 11/1982 | Lewis et al. . |
| 4,506,661 | 3/1985 | Foster . |
| 4,567,887 | 2/1986 | Couch, Jr. .................... 128/118.1 X |
| 4,624,247 | 11/1986 | Ford . |
| 4,628,954 | 12/1986 | Johnson, Jr. . |
| 4,632,098 | 12/1986 | Grundei et al. . |
| 4,634,176 | 2/1987 | Mason et al. . |
| 4,667,672 | 5/1987 | Romanowski .............. 128/DIG. 20 X |
| 4,703,750 | 11/1987 | Sebastian et al. .................... 602/13 |
| 4,805,606 | 2/1989 | McDavid, III . |
| 4,821,707 | 4/1989 | Audette . |
| 4,854,308 | 8/1989 | Drillio . |
| 4,870,956 | 10/1989 | Fatool et al. . |
| 4,872,448 | 10/1989 | Johnson, Jr. . |
| 4,938,207 | 7/1990 | Vargo . |
| 4,940,045 | 7/1990 | Cromartie ............................. 602/26 X |
| 4,999,932 | 3/1991 | Grim . |
| 5,002,045 | 3/1991 | Spademan . |
| 5,022,391 | 6/1991 | Weidenburner . |
| 5,025,575 | 6/1991 | Lakic . |
| 5,025,782 | 6/1991 | Salerno . |
| 5,042,464 | 8/1991 | Skwor et al. . |

(List continued on next page.)

FOREIGN PATENT DOCUMENTS

| | | | |
|---|---|---|---|
| 2627381 | 8/1989 | France ..................................... | 602/16 |
| 2136294 | 9/1984 | United Kingdom . | |

OTHER PUBLICATIONS

Generation II Orthotics USA Inc., *Osteoarthritis Pain–Free Mobility*, 1993, USA.

Omni Scientific, Inc., *Radiograph Engineered Custom Bracing*, 1993, USA.

Primary Examiner—Linda C. M. Dvorak
Attorney, Agent, or Firm—Rodney F. Brown

[57] ABSTRACT

An osteoarthritic knee brace is provided having flexible upper and lower arm members rotatably connected to each other by a rotary hinge assembly. A selectively inflatable or deflatable fluid-containing pad is positionable between the hinge assembly and a side of the knee joint. In operation, the brace is mounted on the leg with the pad engaging both the hinge assembly and the side of the knee joint, the hinge assembly aligned with the knee joint, and the upper and lower arm members aligned with the upper and lower legs, respectively. The upper and lower arm members are stressed away from the knee joint, thereby applying a restoring force to the knee joint across the hinge assembly and the pad that effectively treats the osteoarthritic knee joint. The restoring force is adjustable by selective inflation or deflation of the pad.

24 Claims, 4 Drawing Sheets

U.S. PATENT DOCUMENTS

| | | |
|---|---|---|
| 5,078,128 | 1/1992 | Grim et al. . |
| 5,088,478 | 2/1992 | Grim . |
| 5,107,823 | 4/1992 | Fratesi ................................. 602/26 X |
| 5,113,599 | 5/1992 | Cohen et al. . |
| 5,125,400 | 6/1992 | Johnson, Jr. .............................. 602/13 |
| 5,158,767 | 10/1992 | Cohen et al. . |
| 5,186,163 | 2/1993 | Dye . |
| 5,207,637 | 5/1993 | Janke et al. ................................ 602/26 |
| 5,230,695 | 7/1993 | Silver et al. ............................... 602/13 |
| 5,277,697 | 1/1994 | France et al. ......................... 602/26 X |
| 5,277,698 | 1/1994 | Taylor ....................................... 602/26 |

OSTEOARTHRITIC KNEE BRACE

This application is a continuation-in-part patent application of a co-pending patent application entitled, "Orthopedic Brace Having A System Of Alternately Inflatable Or Deflatable Pneumatic Pads For Adjustable Fitting Of The Brace To The Body", Ser. No 08/104,184 filed on Aug. 10, 1993, now U.S. Pat. No. 5,415,625 which is a continuation-in-part patent application of a patent application entitled, "Orthopedic Brace Having Pneumatic Pads", Ser. No. 07/907,160 filed on Jul. 1, 1992, now U.S. Pat. No. 5,316,547.

TECHNICAL FIELD

The present invention relates generally to an orthopedic brace, particularly to an orthopedic brace for stabilization of a knee joint, and more particularly, though not exclusively, to an orthopedic brace for stabilization of an osteoarthritic knee joint.

BACKGROUND OF THE INVENTION

Osteoarthritis is a degenerative disease of the knee joint which results in chronic pain to the subject when the knee joint is loaded. The pain can be present even when the knee joint is statically loaded, such as when the subject is standing. The pain is particularly apparent, however, when the knee joint is dynamically loaded, such as when the subject is engaging in routine daily activities or exercising.

Although osteoarthritis is commonly held to be a disease of the middle aged or elderly, it also occurs in younger populations, e.g., between about 30 to 40 years of age, as the result of knee joint overuse, injury, or previous surgery. Whereas an elderly individual may have relatively modest dynamic requirements for the knee joint, a younger individual is typically more active and has more rigorous dynamic requirements for the knee joint. Accordingly, any treatment of osteoarthritis must address dynamic as well as static loading of the knee joint.

Osteoarthritic pain is caused by an unbalanced loading on the medial or lateral compartment of the knee joint which closes the clearance space forming the compartment between the condyles of the femur and tibia. When there is contact of the condyles in the respective compartment of the knee joint, and particularly dynamic contact, abrasion occurs at the contact surface producing pain in the joint. Relatively mild osteoarthritic pain can be treated with pain reducing drugs. Invasive surgery, however, has often been the treatment of choice for more advanced cases of osteoarthritis causing debilitating pain. Surgery, nevertheless, may not provide effective long-term correction of the condition because degeneration of the knee joint frequently continues even after initial surgical correction. Accordingly, follow-up surgical procedures can be required to restore and maintain the joint, thereby diminishing the desirability of surgery as a treatment alternative.

As such, a need exists for effective and noninvasive means of relieving pain associated with degenerative diseases of the knee joint, and particularly pain associated with osteoarthritis of the knee joint. U.S. Pat. No. 5,277,698 discloses a brace designed to reduce the effect of osteoarthritis by applying a corrective principle force directly to a single point on the knee joint. The single force point is located posterior to the axis of knee joint rotation on the side of the knee joint opposite the afflicted joint compartment. The principle force is applied by means of a compliant strap contacting the knee joint at the force point. The strap is anchored to the upper and lower leg cuffs of the brace and follows a helical pathway around the knee joint.

Although the brace of U.S. Pat. No. 5,277,698 may reduce the effect of osteoarthritis on the knee joint as the joint approaches full extension, the brace is believed to be ineffective in reducing the effect of osteoarthritis across the entire dynamic range of motion of the knee joint, particularly when the joint is in flexion. The brace of U.S. Pat. No. 5,277,698 is mounted on the leg of a user by presetting the length of the principle force-producing strap. The length is not readily adjustable thereafter as long as the knee joint remains dynamic. Accordingly, the degree of strap tension that can be applied to the knee joint across a range of flexion angles is significantly limited due to slackening of the fixed-length strap at greater flexion angles.

It is nevertheless believed that the greatest treatment benefit to the user is achieved during the swing phase of gait when the knee is flexed and bears no body weight. In this phase it is possible for the corrective force applied by the brace to the knee joint to approach the magnitude of the unbalanced load on the unweighted knee joint, thereby effectively offsetting the imbalance. By comparison, the load on the fully-extended knee joint during the weight-bearing phase of gait is substantially greater than the unweighted load on the knee joint. Osteoarthritic treatment is impractical during the weight-bearing phase because the load on the knee joint is too great to be effectively offset by known braces without applying treatment forces above those tolerable by the user. Thus, any osteoarthritic brace failing to maintain a predictably sustained and tolerable treatment force on the knee joint across the range of flexion angles encountered during the swing gait phase is not an effective treatment means.

UK Patent Application No. GB 2 136 294A discloses a knee brace for treatment of osteoarthritis that substitutes a sling for the helical strap of U.S. Pat. No. 5,277,698 as the principle means of applying the treatment force to the side of the knee joint. Unlike the helical strap, the sling distributes the treatment force across a surface of the joint rather than applying the principle treatment force to a single point posterior to the axis of rotation of the knee joint. The force applied by the sling to the knee joint is nevertheless a function of strap tension because the sling is secured to the brace cuffs by a plurality of straps. Accordingly, the brace of the UK Patent Application is likewise inadequate for dynamic stabilization of an osteoarthritic knee joint.

It is also noted that the braces of UK Patent Application No. GB 2 136 294A and U.S. Pat. No. 5,277,698 both have means for controlling flexion of the knee joint that are connected to the leg cuffs and are positioned on the side of the knee joint opposite the side to which the principle treatment force is applied when the brace is in place on the leg. The knee flexion controlling means are distinguishable from one another, however, insofar as U.S. Pat. No. 5,277,698 employs a rotatable hinge, while UK Patent Application No. GB 2 136 294A employs a piston in parallel with a flexible rod.

U.S. Pat. No. 4,632,098 discloses a knee brace that maintains a padded rigid plate, rather than the above-described sling or strap, in engagement with a side of the knee joint. The brace has a knee rotation controlling means similar to the flexible rod of UK Patent Application No. GB 2 136 294A, but the flexible rod of U.S. Pat. No. 4,632,098 is positioned on the same side of the brace as the knee engaging member, i.e., the plate, and the rod is rigidly connected to the plate and rigid cuffs of the brace. In addition to connection with the rod, the plate is also secured to the brace in an opposing direction by a plurality of flexible straps extending from the plate to the cuffs.

The specific configuration of connectors attaching the plate to the cuffs and rod renders the brace of U.S. Pat. No. 4,632,098 inapplicable to osteoarthritic knee joints. The forces on the plate from the rod and straps tend to cancel one another, preventing the plate from applying an effective treatment force to the side of the knee joint opposite the afflicted compartment of the joint, as required of an osteoarthritic knee brace.

Other knee braces are known in the prior art to provide resilient pads that contact the side of the knee joint as exemplified by U.S. Pat. Nos. 3,581,741 and 5,002,045. The pads, however, merely cushion the leg from the brace while facilitating retention of the brace in position on the leg. The pads primarily exert a tangential frictional force on the side of the knee joint, applying no significant radial treatment force to the side of the joint. The frictional force is incidental to the principle force applied by the cuffs to the upper and lower legs. Like the brace of U.S. Pat. No. 4,632,098, such braces have little relevance to the treatment of osteoarthritis in the knee joint.

It is, therefore, an object of the present invention to provide an orthopedic brace for treatment of degenerative disease in the knee joint, and more particularly for the treatment of osteoarthritis in the knee joint. It is further an object of the present invention to provide an osteoarthritic knee brace that effectively relieves the user of knee joint pain throughout a broad dynamic range of knee joint motion, and particularly in the swing phase of gait. It is another object of the present invention to provide an osteoarthritic knee brace that is readily adjustable to the specific requirements of the user. It is a further object of the present invention to provide an osteoarthritic knee brace that is comfortable for the user to wear and can be worn continuously, if desired, in routine daily activities as well as strenuous physical activities without unduly limiting the mobility of the user. These objects and others are achieved by the invention described hereafter.

SUMMARY OF THE INVENTION

The present invention is an osteoarthritic knee brace positionable on a leg of a user about the knee joint. The brace has a leaf spring comprising an elongated upper arm member and an elongated lower arm member, each arm member having two ends. A rotary hinge assembly rotatably connects the upper and lower arm members to each other at one of their ends. A preformed arcuate upper cuff having two ends is connected at one of its ends to the remaining end of the upper arm member. A preformed arcuate lower cuff having two ends is likewise connected at one of its ends to the remaining end of the lower arm member. Each cuff is aligned such that its diametric axis is substantially orthogonal to the longitudinal axis of the associated arm member. The cuffs are also configured to substantially conform to the circumferential contours of the upper and lower legs of the user, respectively.

The remaining end of the upper cuff includes a longitudinal upper extension member positioned substantially opposite and parallel to the upper arm member. The upper extension member provides the upper cuff with an upper resultant force face on its inner surface that is engagable with the upper leg for applying a first resultant force thereto.

The remaining end of the lower cuff likewise includes a longitudinal lower extension member positioned substantially opposite and parallel to the lower arm member providing the lower cuff with a lower resultant force face on its inner surface that is engagable with the lower leg for applying a second resultant force thereto. The upper arm member and cuff are preferably fabricated as a single integral upper unit and the lower arm member and cuff are likewise preferably fabricated as a single integral lower unit. The upper and lower units are formed from a high-strength material that renders the upper and lower arm members flexible to the extent they are elastically deflectable in a radial direction under a sufficient radial force applied thereto, but are otherwise relatively stiff and resistant to bending.

The brace further includes a resilient pad attached to the inner surface of the hinge assembly and facing the opposing upper and lower resultant force faces of the upper and lower cuffs, respectively. The resilient pad is preferably a substantially hollow bladder, enclosing an interior cavity that is capable of containing a fluid. A selectively resealable valve is provided in the bladder enabling selective fluid communication between the interior cavity and the exterior of the bladder for the addition of fluid into the cavity or withdrawal of fluid from the cavity, thereby enabling selective inflation or deflation of the bladder.

In operation, the brace is mounted on the leg by positioning the upper and lower cuffs on the upper and lower legs, respectively, with the upper and lower resultant force faces engaging the side of the leg proximal to the afflicted knee joint compartment. The resilient pad is engagingly positioned between the hinge assembly and the side of the knee joint opposite the side of the leg engaged by the resultant force faces. The pad is preferably configured to conform to the contours of the side of the knee, having a thickened peripheral portion to substantially encircle the knee condyle and a less thick central portion to receive the knee condyle.

When the brace is freestanding, i.e., not mounted on the leg of a user, the upper and lower arm members of the leaf spring assume an unstressed or undeflected inactive configuration. When the brace is operably mounted on the leg, however, the leaf spring assumes a stressed or deflected active configuration. The degree of spring stress or deflection is adjustable by inflating or deflating the pad. As the pad is inflated, it radially expands and deflects the upper and lower arm members away from the knee joint in a radial direction, thereby increasing the spring restoring force against the knee joint. As the pad is deflated, it radially contracts, enabling the upper and lower arm members to elastically return in the direction of the knee joint, thereby decreasing the spring restoring force against the knee joint.

The actively configured brace effectively stabilizes the osteoarthritic knee joint and reduces the pain of the user by distributing a radially directed treatment force across the pad to the surface of the knee joint engaging the pad. The treatment force is substantially equal to the restoring force of the leaf spring and is sustained throughout the dynamic range of knee joint extension and flexion, particularly as experienced during the swing phase of gait. The treatment force is sufficient to effectively reduce the osteoarthritic knee joint load on the afflicted joint compartment. Resultant forces are simultaneously applied to the upper and lower legs across the resultant force faces in a radial direction opposite that of the treatment force, thereby maintaining the sum of forces on the leg in equilibrium.

The brace is further provided with a plurality of compliant straps that are adjustably secured to the upper and lower units and, in cooperation with the upper and lower units, encircle the upper and lower legs, respectively, when the brace is mounted on the leg. The straps facilitate retention of the brace in proper position about the knee joint during active use of the joint.

The present invention will be further understood, both as to its structure and operation, from the accompanying drawings, taken in conjunction with the accompanying description, in which similar reference characters refer to similar parts.

DESCRIPTION OF PREFERRED EMBODIMENTS

Figure 1:
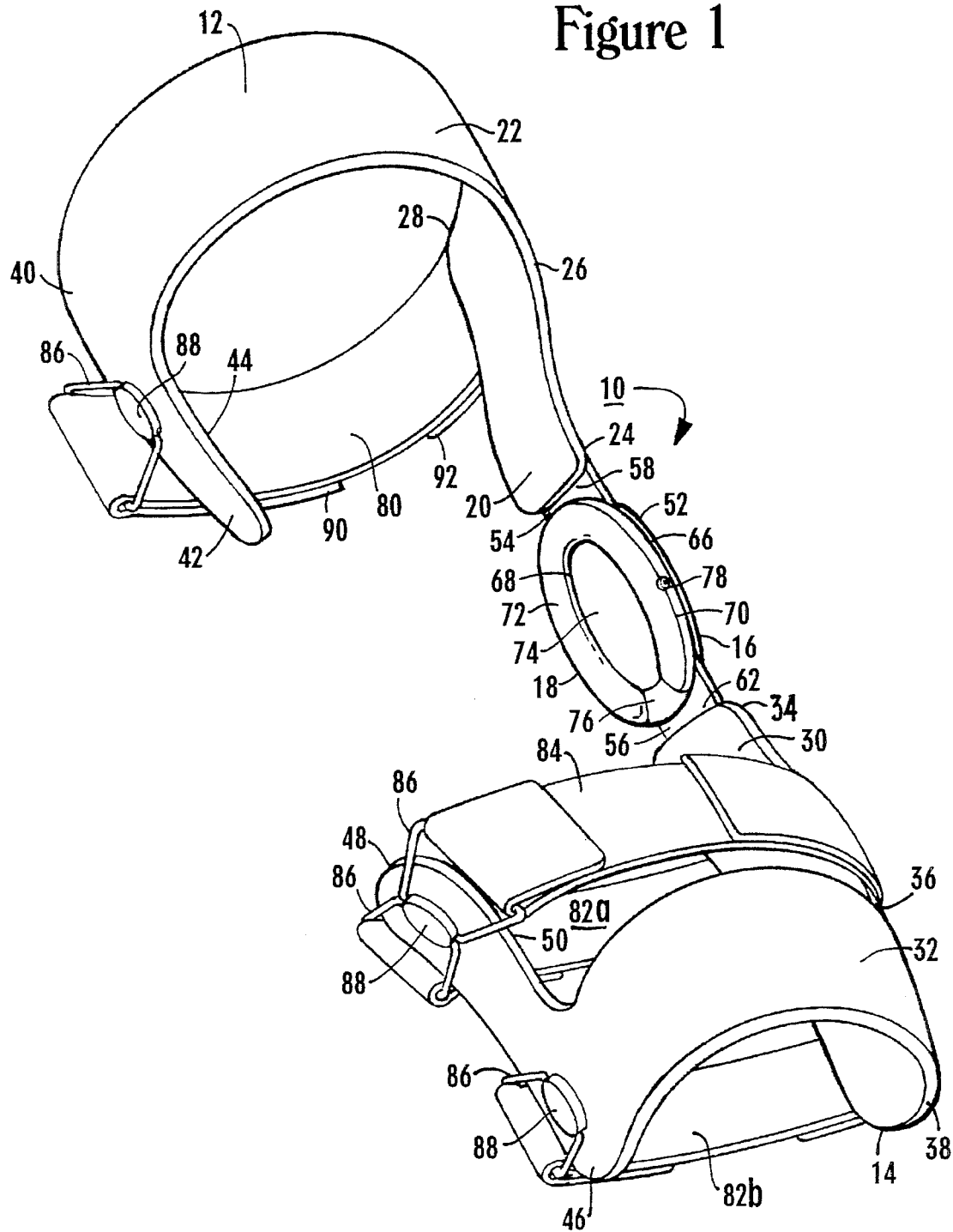
FIG. 1 is a perspective view of an osteoarthritic knee brace of the present invention.

Referring initially to FIG. 1, an osteoarthritic knee brace of the present invention is shown and generally designated 10. The brace 10, shown by way of example, is adapted for placement on the left leg of a user having osteoarthritis of the left knee joint, and in particular afflicting the left medial compartment of the knee joint. The brace 10 comprises an upper unit 12, a lower unit 14, a hinge assembly 16, and a resilient pad 18.

The upper unit 12 is sized to conform to the upper leg of the user and has an integral structure including an upper arm member 20 and an upper cuff 22. The upper arm member 20 has an elongate shape with a proximal end 24 and a distal end 26 relative to the hinge assembly 16. The proximal end 24 is fixably and rigidly secured to the hinge assembly 16 while the distal end 26 is integrally connected to a proximal end 28 of the upper cuff 22.

The lower unit 14 has substantially the same integral structure as the upper leg unit 12, but is sized to conform to the lower leg of the user. Accordingly, the lower unit 14 has a lower arm member 30 and a lower cuff 32. The lower arm member 30 has an elongate shape with a proximal end 34 and a distal end 36. The proximal end 34 is fixably and rigidly secured to the hinge assembly 16 while the distal end 36 is integrally connected to a proximal end 38 of the lower cuff 32. In combination, the upper and lower arm members 20, 30 connected via the hinge assembly 16 comprise a leaf spring as is described hereafter.

The upper cuff 22 has a preformed arcuate shape sized to snugly conformingly engage the anterior portion of the thigh. As noted above, the proximal end 28 of the upper cuff 22 is integrally connected to the distal end 26 of the upper arm member 20. The upper cuff 22 extends away from the upper arm member 20 with the diametric axis of the upper cuff 22 aligned substantially orthogonal to the longitudinal axis of the upper arm member 20. The distal end 40 of the upper cuff 22 includes an upper extension member 42 extending in a proximal direction and having its longitudinal axis in substantially parallel alignment with the longitudinal axis of the upper arm member 20. The inner face of the upper extension member 42 forms an upper resultant force face 44 opposing the inner face of the upper arm member 20.

The lower cuff 32 has substantially the same configuration as the upper cuff 22, but the preformed arcuate shape thereof is sized somewhat smaller to snugly conformingly engage the anterior shin portion of the lower leg. The proximal end 38 of the lower cuff 32 integrally connects to the distal end 36 of the lower arm member 30. The lower cuff 32 extends away from the lower arm member 30 with the diametric axis of the lower cuff 32 aligned substantially orthogonal to the longitudinal axis of the lower arm member 30. The distal end 46 of the lower cuff 32 includes a lower extension member 48 extending in a proximal direction and having its longitudinal axis in substantially parallel alignment with the longitudinal axis of the lower arm member 30. The inner face of the lower extension member 48 forms an upper resultant force face 50 opposing the inner face of the lower arm member 30.

The upper and lower arm members 20, 30 are formed from a high-strength, flexible material such that the arm member elastically deflects when a sufficient force is applied to an end of the arm member in a direction orthogonal to the longitudinal axis of the arm member. In the absence of such a force, the upper and lower arm members 20, 30 are relatively stiff and generally resistant to bending. Materials satisfying these criteria include certain metals, ceramics, plastics, and composites. A preferred material is a thermoplastic composite such as a polypropylene polymer or copolymer having reinforcing glass filaments embedded therein. In a preferred embodiment, the entire upper unit 12 is unitarily formed from the same flexible material. The lower unit 14 is likewise unitarily formed from the same material.

The upper and lower arm members 20, 30 are rotatably connected to one another by means of the rotary hinge assembly 16. The hinge assembly 16 comprises a hinge cover 52, an upper rotary connector 54 and a lower rotary connector 56. The cover 52 and connectors 54, 56 are formed from one or more high-strength, rigid materials, such as metals or plastics. Connection of the upper and lower arm members 20, 30 is effectuated by fixably securing the proximal end 24 of the upper arm member 20 to the distal end 58 of the upper rotary connector 54 by means such as thermally molding the proximal end 24 to enclose the distal end 58. The proximal end 34 of the lower arm member 30 is similarly fixably secured to the distal end 62 of the lower rotary connector 56. The upper and lower connectors 54, 56 have conventional semi-circular proximal ends (not shown) that are pivotally anchored within the hinge cover 52 by pivot pins and are provided with interlocking teeth. This construction of the hinge assembly 16 enables rotatable engagement of the upper and lower rotary connectors 54, 56, and correspondingly enables rotation of the upper and lower units 12, 14 relative to each other.

The hinge cover 52 has a substantially planar inner face 66 directed toward the upper and lower resultant force faces 44, 50 of the upper and lower cuffs 22, 32, respectively. The resilient pad 18 is releasably fastened to the inner face 66 by conventional releasable fastening means such as a hook and loop fastener coupling, commonly termed VELCRO, wherein one element of the coupling is substantially permanently affixed to the inner face 66 and the other element of the coupling is substantially permanently affixed to the resilient pad 18. The pad 18, in its preferred embodiment, has a substantially similar configuration to the hinge pads taught by U.S. patent application Ser. No. 08/104,184, which issued as U.S. Pat. No. 5,816,547 incorporated herein by reference.

The pad 18 overlies the planar inner face 66 of the hinge cover 52, but has surface contours providing the pad 18 with a toroidal configuration defined by an inner perimeter 68 and an outer perimeter 70. The peripheral portion 72 of the pad 18 between the inner and outer perimeters 68, 70 has a greater thickness than the central portion 74 of the pad 18 within the inner perimeter 68. The central portion 74 can simply be a void space, or can alternatively be formed from a dimensionally thinner piece of the same, or a different, material as the peripheral portion 72.

In any case, the toroidal configuration of the pad 18 enables the peripheral portion 72 to encircle the apex of a knee condyle while the central portion 74 receives the apex of the knee condyle when the brace 10 is mounted on the leg of the user, thereby facilitating conformance of the pad 18 with a side of the knee joint. The peripheral portion 72 may also include an indented section 76 at its lower end to minimize pressure from the pad 18 against the fibular head and the common peroneal nerve when the pad 18 engages the lateral side of the knee joint. Like the central portion 74, the indented section 76 can simply be a void space, or can alternatively be formed from a dimensionally thinner piece of the same, or a different, material as the peripheral portion 72.

The pad 18 may have any number of constructions satisfying the above-described configuration. For example, the pad 18 can have a continuous solid construct using such resilient materials as elastomers, expanded foams, or felt. In its preferred embodiment, however, the pad 18 has the construction as shown in FIG. 1 herein and substantially as taught by U.S. patent application Ser. No. 08/104,184. Accordingly, the peripheral portion 72 of the pad 18 is preferably a hollow bladder constructed from a fluid-impermeable, thin, elastic outer skin. The bladder is fabricated by joining two sheets of the skin along the inner and outer perimeters 68, 70 to form seams that enclose an interior cavity capable of retaining a fluid. The central portion 74 and indented segment 76 can be either a hollow bladder, a continuous solid material or a void, subject to the limitation that each is thinner than the peripheral portion 72. A garment material, such as natural or synthetic cloth or leather, may further be affixed to the skin of the pad to enhance the comfort of the user. Synthetic chamois is a preferred garment material.

The peripheral portion 72 is inflatable or deflatable by means of a selectively sealable valve 78 penetrating the seam along the outer perimeter 70 of the peripheral portion 72. The valve 78 permits selective fluid communication between the interior and exterior of the cavity enclosed within the peripheral portion 72. The valve 78 is preferably biased in the closed position and opened by insertion of a pump needle (not shown) therein. A detachable pump (not shown) or a pump (not shown) integral with the valve 78 can be used to inflate the pad 18. Teaching of such pumps and valves is conventional and, thus, well known to those skilled in the art.

A preferred fluid for injection by means of a pump into the interior cavity of the peripheral portion 72 in the manner set forth above is a compressible fluid, more preferably a gas, and most preferably air at ambient atmospheric conditions. The injection of other gaseous, liquid or gel-like fluids, however, is possible within the scope of the present invention. It is further understood that the injected fluid can conversely be withdrawn from the interior cavity of the peripheral portion 72 by opening the valve 78 and displacing the fluid from the cavity through the valve 78 into the exterior of the cavity.

The brace 10 further comprises a system of adjustable straps to maintain the upper and lower units 12 and 14 in a desired position on the leg of the user, particularly when the user is physically active. The strap system comprises an upper posterior strap 80 engaging the upper unit 12, and a pair of lower posterior straps 82a, 82b and a lower anterior strap 84 engaging the lower unit 14. Associated with each strap 80, 82a, 82b, 84 is a pair of strap loops (a first strap loop of each pair is shown in FIG. 1 and designated 86). Each strap loop 86 is fixably attached to the upper or lower unit 12, 14 by a retention button 88. The strap loops 86 are preferably fabricated from a rigid metal and the straps 80, 82a, 82b, 84 are preferably fabricated from a compliant, but inelastic, natural or synthetic cloth.

Figure 2:
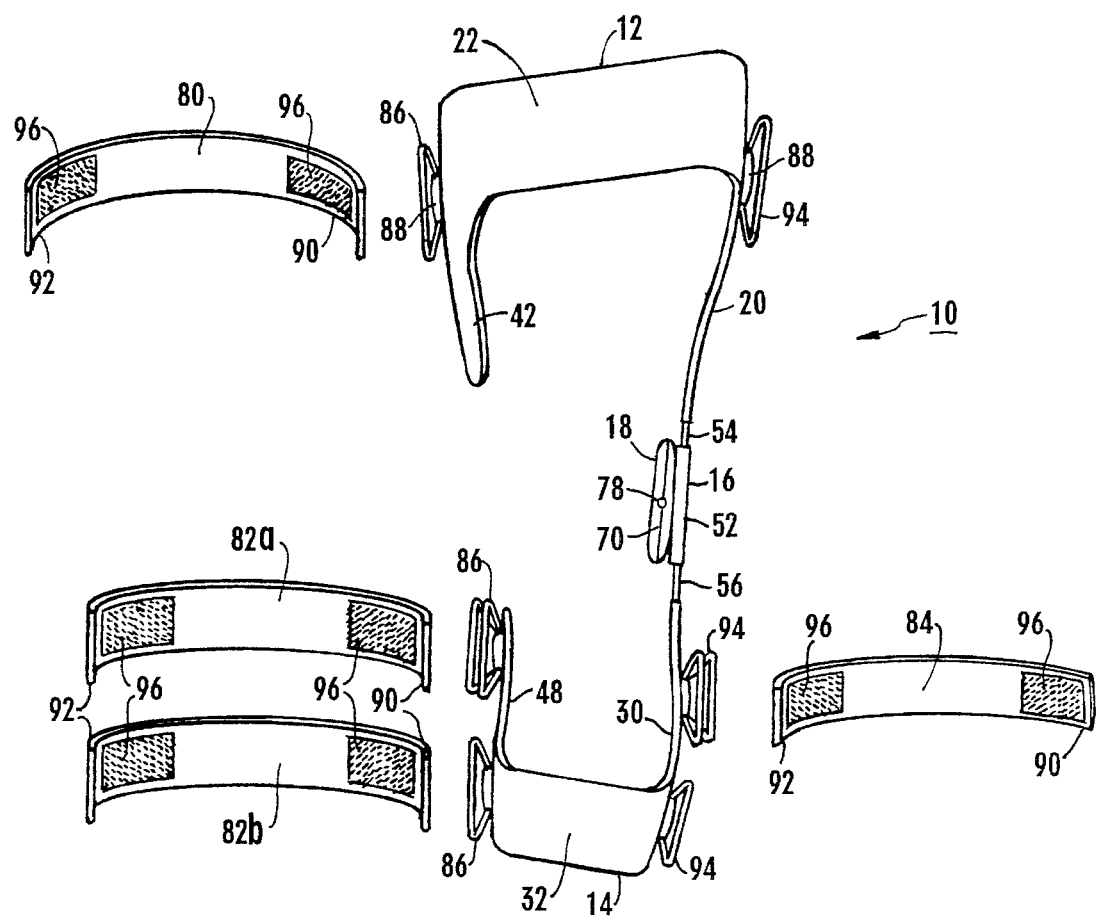
FIG. 2 is a frontal view of the osteoarthritic knee brace of FIG. 1.

Referring to FIG. 2 along with FIG. 1, the upper posterior strap 80 is shown to have a first end 90 removably attachable to the first strap loop 86 and a second end 92 removably attachable to a second strap loop 94 of the pair associated with the strap 80. The first and second ends 90, 92 are each provided with a releasable hook and loop fastener 96. The upper posterior strap 80 forms a continuous enclosure in cooperation with the upper unit 12 when the first and second ends 90, 92 are looped through their associated first and second strap loops 86, 94, respectively, and the ends 90, 92 are fastened back onto themselves by means of the hook and loop fasteners 94 in a manner apparent to the skilled artisan. The lower straps 82a, 82b, 84 are likewise provided with associated second strap loops and hook and loop fasteners enabling the lower straps 82a, 82b, 84 to form a continuous enclosure in cooperation with the lower unit 14 in substantially the same manner as described above with respect to the upper posterior strap 80.

Although not shown in the drawings, the inner surfaces of the upper and lower units 12, 14 can be provided with detachable resilient padding having a fluid-containing construct or a continuous solid construct using such resilient materials as elastomers, expanded foams, or felt. The detachable padding cushions the leg from the relatively hard surfaces of the upper and lower units 12, 14 for the added comfort of the user. The straps 80, 82a, 82b, 84 may likewise be provided with such padding to cushion the leg therefrom.

Referring again to FIG. 2, the brace 10 is shown in a freestanding position unmounted on the leg. The leaf spring comprising the upper and lower arm members 20, 30 is an inactive configuration, wherein the arm members 20, 30 are unstressed. Upper and lower units 12, 14 are both shown to have a tapered configuration, wherein the upper and lower arm members 20, 30 have a preformed proximally inward curve, i.e., concave, in the direction of the hinge assembly 16, thereby conforming to the longitudinal contours of the upper and lower legs, respectively. It is understood, however, that other preformed configurations of the arm members 20, 30 are within the scope of the present invention, including straight or convex configurations. The straps 80, 82a, 82b, 84 are also shown in an unfastened condition removed from their associated first and second strap loops 86, 94.

METHOD OF OPERATION

Figure 3:
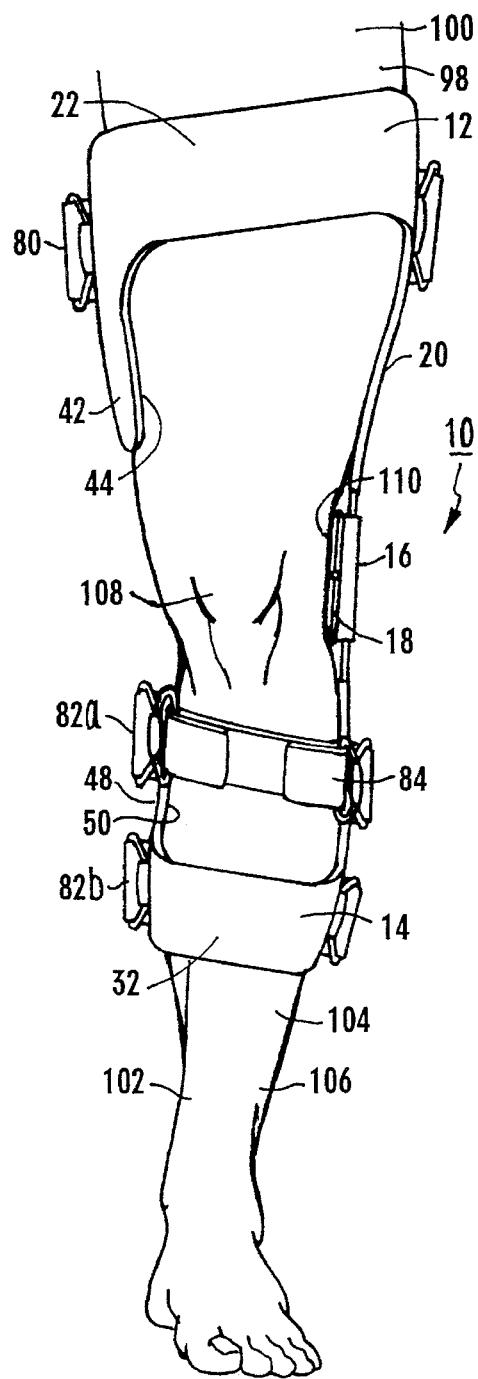
FIG. 3 is a perspective view of the osteoarthritic knee brace of FIG. 1 mounted on the extended leg of a user with the spring adjusted to apply a relatively low treatment force to the knee joint.

Operation of the brace 10 is described with reference to FIGS. 3 and 4. Referring initially to FIG. 3, the brace 10 is shown mounted on the left leg 98 of the user and applying a relatively low treatment force thereto. To mount the brace 10 on the leg 98, the upper cuff 22 including the upper extension member 42 is placed anteriorly over the upper leg 100 in fitted engagement therewith, such that the upper resultant force face 44 of the upper extension member 42 snugly engages the upper leg 100 at the medial side of the leg 102. In a similar manner, the lower cuff 32 including the lower extension member 48 is placed anteriorly over the lower leg 104 in fitted engagement therewith, such that the lower resultant force face 50 of the lower extension member 48 snugly engages the lower leg 104 at the medial side.

With the upper and lower cuffs 22, 32 positioned on the upper and lower legs 100,104, respectively, and the upper and lower resultant force faces 44, 50 positioned against the medial side of the leg 102, the arm members 20, 30 and hinge assembly 16 are correspondingly positioned adjacent to the lateral side of the leg 106 with the pad 18 in snug fitting engagement with the lateral side of the leg 106, and more particularly with the knee joint 108 on the lateral side of the leg 106. It is noted that the outer perimeter 70 of the pad 18 typically has a length on the order of about 3 inches or more and a width on the order of about 2 inches or more, such that the pad 18 engages the knee joint 108 across a substantial area of the lateral knee joint surface 110 encircling the lateral knee condyle and applies a treatment force to the engaged area.

With the pad 18 partially deflated, as shown in FIG. 3, the sum of the forces applied by the leaf spring 20, 30 to the lateral knee joint surface 110 in a medial radial direction and applied by the upper and lower extension members 42, 50 to the medial side 102 of the upper and lower legs 100, 104 in the lateral radial direction may be sufficient to substantially retain the brace 10 in place on the leg 98. The straps 80, 82a, 82b, 84 are provided, however, to further insure that the position of the brace 10 is properly retained on the leg 98 during vigorous exercise thereof. Accordingly, the final step of mounting the brace 10 on the leg 98 is to draw the upper strap 80 around the upper leg 100 above the knee joint 108, draw the lower straps 82a, 82b, 84 around the lower leg 104 below the knee joint 108 and secure them to the upper and lower units 12, 14, respectively, in the manner previously described.

Figure 4:
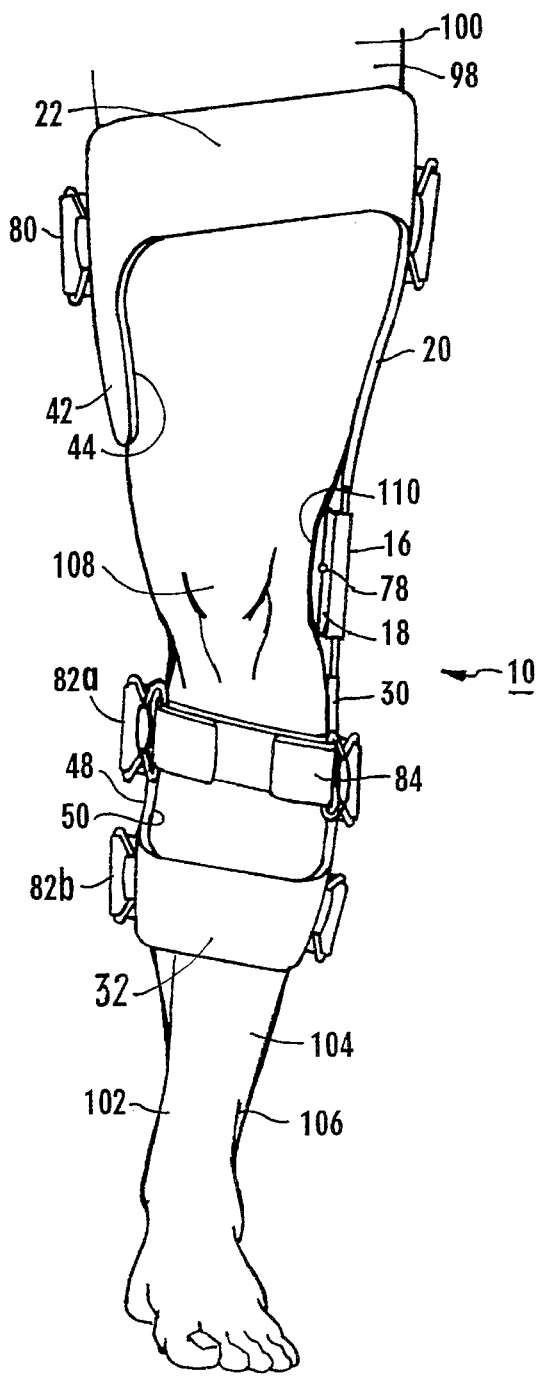
FIG. 4 is a perspective view of the osteoarthritic knee brace of FIG. 1 mounted on the extended leg of a user with the spring adjusted to apply a relatively high treatment force to the knee joint.

Referring to both FIGS. 3 and 4, it is shown that the treatment force applied by the brace 10 to the leg 98 in the radial medial direction, which corresponds to the restoring force of the leaf spring 20, 30, is adjustable with the brace 10 mounted on the leg 98. In particular, it is shown that the treatment force applied to the lateral surface of the knee joint 110 is increased by inflating the pad 18 to the greater thickness shown in FIG. 4 and decreased by deflating the pad 18 to the lesser thickness shown in FIG. 3. The pad 18 is inflated by pumping a desired fluid into the pad 18 via the valve 78, and the pad 18 is conversely deflated by withdrawing resident fluid from the pad 18 via the valve 78.

When the pad thickness is increased, the stressed arm members 20, 30 of the leaf spring deflect a substantial distance in the radial lateral direction away from the lateral surface of the knee joint 110, as shown in FIG. 4. A relatively high degree of deflection causes the leaf spring 20, 30 to apply a relatively high treatment force in the radial medial direction to the lateral knee joint surface 110 across the pad 18 that corresponds to the spring restoring force. At the same time, the resultant force faces 44, 50 apply opposing resultant forces to the medial side 102 of the upper and lower legs 100, 104 above and below the knee joint 108 that equilibrate the sum of forces on the leg 98, and maintain the brace 10 static relative to the leg 98. The relatively high treatment force focused by the pad 18 on the lateral knee joint surface 110, however, significantly reduces the unbalanced load on the osteoarthritic medial compartment of the knee joint 108, thereby alleviating the pain of the user.

Being a dynamic system, the treatment force applied by the spring 20, 30 to the knee joint may have some inherent variability over the entire range of knee joint motion. It is nevertheless apparent that the brace 10 continuously applies an effective treatment force to the lateral side of the knee joint 110, not only at full extension as shown herein, but at substantially any dynamic or static flexion or extension angle of the knee joint 108, and particularly at the flexion angles experienced during the swing phase of gait.

As an example of operation, the brace of the present invention, as shown in FIG. 1, was laterally mounted on the left leg of a user in the above-described manner with substantially all fluids removed from the pad. Although the spring exhibited little deflection in the lateral direction when compared to the unmounted brace, the pad applied a radial force of 4 pounds to the lateral knee joint surface in the medial direction. The pad was then inflated substantially to capacity with ambient air. The spring thereafter exhibited a radial deflection of 0.30 inches from its previous position in the lateral direction, and the pad applied a radial force of 24 pounds to the lateral knee joint surface in the medial direction.

Although the above-recited example is not to be construed as limiting the scope of the present invention, the example indicates that braces can be constructed in accordance with the present invention that provide a broad range of adjustability for applying treatment forces to the knee joint. It is apparent that the skilled artisan can modify the range of adjustability of the braces within the scope of the present invention inter alia by selecting materials of different elasticity for construction of the arm members, by selecting different longitudinal or cross-sectional dimensions for the arm members, or by selecting pads of different fixed thicknesses or different ranges of adjustable thicknesses.

It is further evident that although the brace of the present invention has only been described above in terms of an embodiment adapted to treat osteoarthritis in the medial compartment of the left knee joint, it is apparent to the skilled artisan that this embodiment is readily adaptable to treatment of osteoarthritis in either the lateral or medial compartments of either the right or left knee joints by obvious modifications of the embodiment within the scope of the present invention. It is also apparent to the skilled artisan that the embodiment described herein can be reconfigured within the scope of the present invention by reversing the anterior orientation of either or both the upper and lower cuffs.

Figure 5:
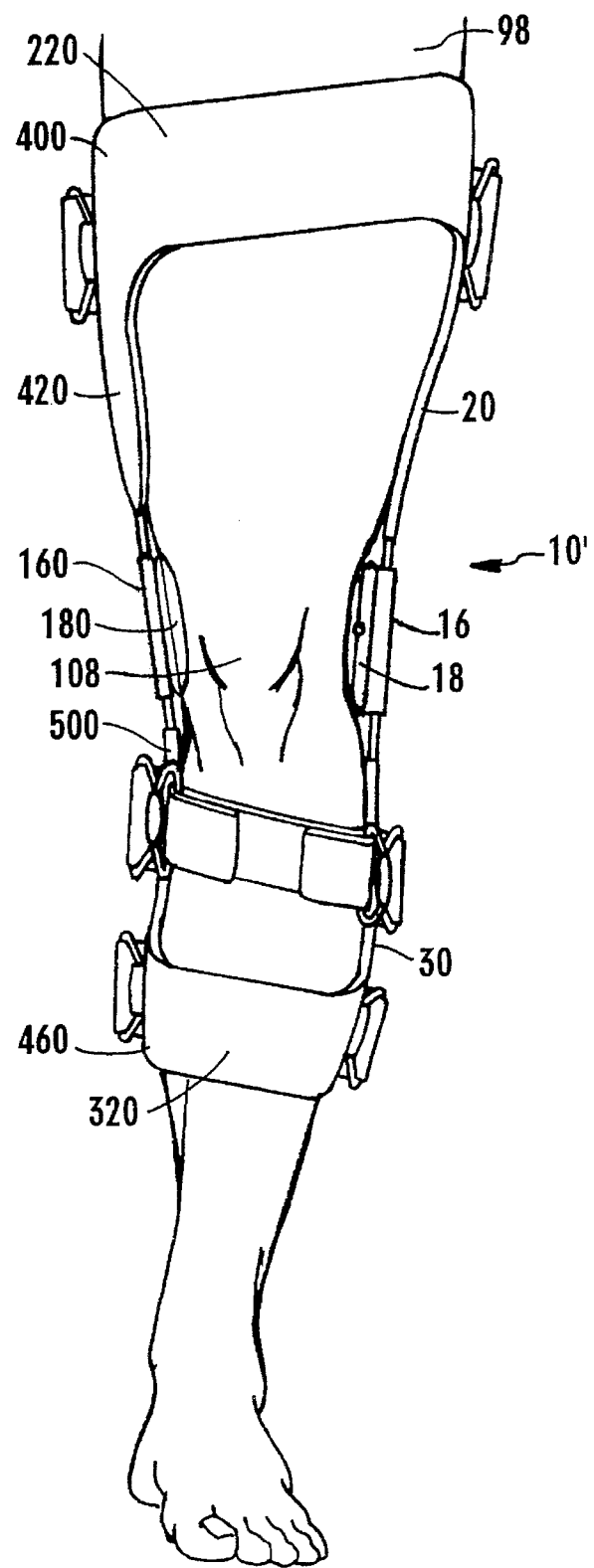
FIG. 5 is a perspective view of an alternate embodiment of an osteoarthritic knee brace of the present invention mounted on the extended leg of a user with the spring adjusted to apply a relatively high treatment force to the knee joint.

Yet another embodiment of the brace of the present invention is described with reference to FIG. 5. The alternate brace is shown and generally designated 10'. The brace 10' is substantially identical to the brace 10 of FIG. 1 except that the discontinuous extension members 42, 50 of brace 10 are replaced in brace 10' by extension arms 420, 500 and a connective rotary hinge assembly 160 that extend continuously in series from the distal end 400 of the upper cuff 220 to the distal end 460 of the lower cuff 320. The extension arms 420, 500 and hinge assembly 160 are substantially mirror images of the arm members 20, 30 and hinge assembly 16.

The primary function of the extension arms 420, 500 and connective rotary hinge assembly 160, in addition to assuming the function of the extension members 42, 50, is to provide the knee joint 108 with added anterior/posterior and medial/lateral stability during physical activity without substantially altering the balance of radial forces applied by the brace 10' to the knee joint 108. Accordingly, the extension arms 420, 500, in conjunction with a pad 180 provided on the inner face of the hinge assembly 160, are configured to avoid substantial radial flexion when the brace 10' is mounted on the leg 98. The pad 180 functions to cushion the knee joint 108 from the rigid hinge assembly 160 rather than to apply a radial force to the knee joint 108. Since any radial force applied to the knee joint 108 across the pad 180 is small relative to the opposing radial force applied across the pad 18, the effect of such a force is negligible and does not impair the treatment effect of the radial force applied across the pad 18.

While the forgoing preferred embodiments of the invention have been described and shown, it is understood that alternatives and modifications, such as those suggested and others, may be made thereto and fall within the scope of the invention.

We claim:

1. An osteoarthritic knee brace positionable on a leg about the knee joint comprising:

means for engaging the knee joint at a first side of the leg opposite a second side of the leg; and means for continuously applying a spring restoring force to the knee joint at said first side of the leg across said knee joint engagement means thereby elastically deflecting said spring restoring force application means in a direction away from the knee joint at said first side of said leg, wherein said spring restoring force is sufficient to reduce a load on a compartment of the knee joint proximal to said second side of the leg.

2. A knee brace as recited in claim 1 further comprising means for applying a first resultant force to the upper leg at said second side of the leg to resist said spring restoring force.

3. A knee brace as recited in claim 1 further comprising means for applying a second resultant force to the lower leg at said second side of the leg to resist said spring restoring force.

4. A knee brace as recited in claim 1 further comprising means for rotating said first resultant force applying means relative to said second resultant force applying means about the knee joint, wherein said rotating means is positionable proximal to the knee joint at said first side of the leg.

5. A knee brace as recited in claim 1 wherein said knee joint engagement means comprises a resilient pad.

6. A knee brace as recited in claim 5 wherein said knee joint engagement means is further a means for adjusting said spring restoring force by adjusting the thickness of said pad.

7. A knee brace as recited in claim 1 wherein said knee joint engagement means is an inflatable or deflatable fluid-containing bladder.

8. A knee brace as recited in claim 7 wherein said knee joint engagement means is further a means for adjusting said spring restoring force by inflating or deflating said bladder.

9. A knee brace as recited in claim 1 wherein said knee joint engagement means is further a means for conformingly engaging a condyle of the knee joint.

10. An osteoarthritic knee brace positionable on a leg about the knee joint comprising:

a spring comprising a flexible upper arm member and a flexible lower arm member, said spring having an active configuration when positioned on a leg about a knee joint and an inactive configuration when removed from the leg;

a hinge rotatably connecting said upper and lower arm members; and a pad engaging said hinge and engagable with the knee joint on a first side of the leg opposite a second side of the leg, wherein said spring has an elastic deflection distance in a direction away from said pad and a restoring force in a direction toward said pad in said active configuration.

11. A knee brace as recited in claim 10 further comprising a preformed arcuate upper cuff connected to said upper arm member and engagable with the upper leg at said second side of the leg.

12. A knee brace as recited in claim 10 further comprising a preformed arcuate lower cuff connected to said lower arm member and engagable with the lower leg at said second side of the leg.

13. An osteoarthritic knee brace as recited in claim 10 wherein said spring has a restoring force in said active configuration sufficient to reduce a load on a compartment of the knee joint proximal to said second side of the leg.

14. An osteoarthritic knee brace as recited in claim 10 wherein said pad has an adjustable thickness.

15. An osteoarthritic knee brace as recited in claim 10 wherein said pad is an inflatable or deflatable fluid-containing bladder.

16. An osteoarthritic knee brace positionable on a leg about the knee joint comprising:

a spring comprising a flexible upper arm member and a flexible lower arm member;

a hinge rotatably connecting said upper and lower arm members; and a resilient pad having an adjustable thickness, engaging said hinge, and in connective association with said upper arm member and said lower arm member, further wherein said pad is engagable with the knee joint on a first side of the leg opposite a second side of the leg.

17. A knee brace as recited in claim 16 wherein said resilient pad is an inflatable or deflatable fluid-containing bladder.

18. A method for stabilizing an osteoarthritic knee comprising mounting a brace on a leg about the knee joint, wherein said brace has a flexible upper arm positioned above the knee joint and a flexible lower arm positioned below the knee joint and connected to said upper arm that are elastically deflected by the leg in a direction away from the knee joint, thereby continuously applying a spring restoring force to the knee joint on a first side of the leg sufficient to reduce a load on a compartment of the knee joint proximal to a second side of the leg, further wherein said spring restoring force is substantially orthogonal to said load.

19. A method for stabilizing a knee as recited in claim 18 wherein said spring restoring force is applied to the knee joint across a resilient pad.

20. A method for stabilizing a knee as recited in claim 18 wherein said spring restoring force is applied to the knee joint across an inflatable or deflatable fluid-containing bladder.

21. A method for stabilizing a knee as recited in claim 20 wherein said spring restoring force is decreased by deflating said bladder and said spring restoring force is increased by inflating said bladder.

22. A method for stabilizing a knee as recited in claim 18 further comprising applying a first resultant force against the upper leg at a second side of the leg opposite said first side to resist said spring restoring force.

23. A method for stabilizing a knee as recited in claim 18 further comprising applying a second resultant force against the lower leg at said second side of the leg to resist said spring restoring force.

24. A method for stabilizing an osteoarthritic knee as recited in claim 18 wherein said spring restoring force is continuously applied to said knee joint during the swing phase of gait.

* * * * *